United States Patent
Green et al.

(10) Patent No.: US 6,833,374 B2
(45) Date of Patent: Dec. 21, 2004

(54) DIHYDROPYRAZOLO[3,4-D]THIENO[2,3-B] PYRIDINONE INHIBITORS OF B7-1

(75) Inventors: Neal Jeffrey Green, Newton, MA (US); Lihren Chen, Cambridge, MA (US); Steve Yikkai Tam, Wellesley, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/629,022

(22) Filed: Jul. 28, 2003

(65) Prior Publication Data
US 2004/0024009 A1 Feb. 5, 2004

Related U.S. Application Data

(60) Provisional application No. 60/399,225, filed on Jul. 29, 2002.

(51) Int. Cl.[7] .................. A61K 31/4353; C07D 495/12
(52) U.S. Cl. .......................................... 514/293; 546/83
(58) Field of Search ............................. 514/293; 546/83

(56) References Cited

U.S. PATENT DOCUMENTS

| 4,560,689 A | 12/1985 | Yokoyama |
| 4,814,450 A | 3/1989 | Yokoyama |
| 6,107,304 A | 8/2000 | Luengo |

OTHER PUBLICATIONS

Ian T. Forbes et al., Journal of Medicinal Chemistry, 1990, vol. 33, 2640–2645.

*Primary Examiner*—Charanjit S. Aulakh
(74) *Attorney, Agent, or Firm*—Barbara L. Lences

(57) ABSTRACT

The present invention provides a compound of formula I and the use thereof for the immunotherapeutic treatment of transplant rejection, autoimmune disease or graft vs. host disease.

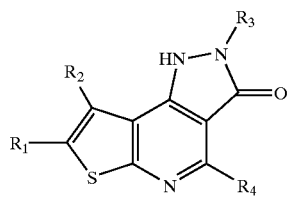

(I)

20 Claims, No Drawings

DIHYDROPYRAZOLO[3,4-D]THIENO[2,3-B] PYRIDINONE INHIBITORS OF B7-1

This application claims priority from copending provisional application Ser. No. 60/399,225, filed Jul. 29, 2002, the entire disclosure of which is hereby incorporated by reference.

BACKGROUND OF THE INVENTION

Regulation of T cell responses plays a primary role in determining the outcome of auto-immune disease, the development of tumor immunity, and graft survival following transplantation (Bluestone, et.al. *Annu, Rev. Immunol.* 1996, 14, 233–258.; Kuchroo, et. al. *Crit. Rev. Immunol.* 1998, 18, 389–418.; Guinan, et. al. *N. Engl. J. Med.* 1999, 340, 1704–1714.; Abrams et. al. *J. Exp. Med.* 2000, 192, 681–694). These immune responses are controlled by the interaction of molecules on T cell and antigen presenting cell surfaces. Activation of T cells requires two signals, an antigen-specific signal delivered through T cell antigen receptor, and a second co-stimulatory signal. This co-stimulatory signal dictates the outcome for T cells through the binding of B7-1 and B7-2 expressed on antigen presenting cells to CD28 and CTLA-4 on T cells. CD28 engagement by B7-1 or B7-2 amplifies T cell receptor signaling and stimulates production of cytokines required for T-cell proliferation. On the other hand, CTLA-4 engagement by B7-1 or B7-2 down regulates the immune response (Allison, et. al. *Nature* 1992, 356, 607–609.; Bluestone, et. al. *Immunity* 1994, 1, 405–413.; Thompson, et. al. *Science* 1995, 270, 985–988). In experimental disease models, altering these co-stimulatory signals has profound effects on immunity. Blocking B7/CD28 interactions with monoclonal antibodies or soluble receptors results in immunosuppression and enhanced allograft survival, while B7/CTLA-4 blockade results in enhanced anti-tumor immune responses (Larsen, et. al. *Nature* 1996, 381, 434–438). Consequently, agents, such as small molecules, which act as inhibitors of cell-cell interactions may be useful in the development of effective immunomodulatory medicines.

Therefore, it is an object of this invention to provide compounds which are useful as immunotherapeutic agents in the treatment of transplant rejection, autoimmune disease or graft vs host disease.

It is another object of this invention to provide therapeutic methods and pharmaceutical compositions useful for the treatment of transplant rejection, autoimmune disease or graft vs host disease.

It is a feature of this invention that the compounds provided may be used to further study and elucidate the interactions of B7-1 with the CD28 receptor.

These and other objects and features of the invention will become more apparent by the detailed description set forth hereinbelow.

SUMMARY OF THE INVENTION

The present invention provides a compound of formula I:

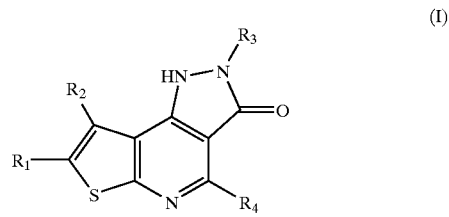

wherein $R_1$ and $R_2$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_3$ is H, $C_1$–$C_6$alkyl optionally substituted with a phenyl, naphthyl or heteroaryl group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CONR_{15}R_{16}$, $SO_2NR_{15}R_{16}$, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or heteroaryl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_4$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_5$ is H, $C_1$–$C_3$alkyl or haloalkyl;

$R_6$, $R_9$, $R_{12}$, $R_{17}$, $R_{20}$, $R_{26}$ and $R_{27}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

n is 0 or an integer of 1 or 2;

$R_7$, $R_8$, $R_{10}$, $R_{11}$, $R_{13}$, $R_{14}$, $R_{18}$, $R_{19}$, $R_{21}$, R22, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; and $R_{15}$ and $R_{16}$ are each independently H, $NH_2$, $CH_2CH_2OCH_2CH_2OCH_2CH_2NH_2$ or a $C_1$–$C_6$alkyl group optionally substituted with one or two CN, $OR_5$, $NR_{13}R_{14}$, $CO_2R_{17}$ or $C_3$–$C_7$cycloalkyl group;

phenyl optionally substituted with one or two halogen, $OR_5$, CN, $NR_{13}R_{14}$, $CO_2R_{17}$, $COR_{27}$, an optionally substituted $C_1$–$C_8$alkyl group or an optionally substituted $C_2$–$C_6$alkenyl group;

benzyl optionally substituted with one or two halogen, $OR_5$, $COR_{27}$ or a $C_1$–$C_6$alkyl group optionally substituted with one $OR_5$ or pyridinyl optionally substituted with one or two halogen, $OR_5$, $NR_{13}R_{14}$ or $CO_2R_{17}$ groups or $R_{15}$ and $R_{16}$ may be taken together with the atom to which they are attached to form an optionally substituted 5- to 7-membered ring optionally containing one double bond, a benzofused ring or an additional heteroatom selected from O, N or S; or the stereoisomers thereof or the pharmaceutically acceptable salts thereof.

The present invention also provides methods and compositions useful for the immunotherapeutic treatment of transplant rejection, autoimmune disease or graft vs host disease.

DETAILED DESCRIPTION OF THE INVENTION

Full T cell activation requires both an antigen-specific and a second co-stimulatory signal. Co-stimulation dictates the outcome for T cells through the binding of B7-1 and B7-2 expressed on antigen-presenting cells to CD28 and CTLA4 on T cells (Greenfield, E. A., Nguyen, K. A. and Kuchroo, V. K. (1998) Critical Review of Immunology, 18, 389–418 and Lenschow, D. J., Walunas, T. L. and Bluestone, J. A. (1996) Annual Review of Immunology, 14, 233–258). Animal studies and clinical trials with protein antagonists of these interactions indicate considerable promise for immunotherapy in transplantation and autoimmune disease.

Surprisingly, it has now been found that dihydropyrazolo[3,4-d]thieno[2,3-b]pyridinone compounds of formula I are effective inhibitors of B7-1/CD28 binding. Equilibrium dialysis demonstrates that compounds of formula I bind specifically to human B7-1 at a common site. Occupancy of this site by said inhibitors blocked B7-1 binding not only to CD28, but also to CTLA-4 (although at much higher concentrations of inhibitor). Accordingly, the present invention provides dihydropyrazolo[3,4-d]thieno[2,3-b]pyridinone B7-1 inhibitors of formula I:

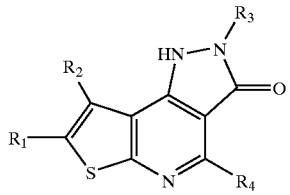

(I)

wherein $R_1$ and $R_2$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_3$ is H, $C_1$–$C_6$alkyl optionally substituted with a phenyl, naphthyl or heteroaryl group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CONR_{15}R_{16}$, $SO_2NR_{15}R_{16}$, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or heteroaryl optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_4$ is phenyl optionally substituted with one to three halogen, $NO_2$, CN, hydroxy, $C_1$–$C_6$alkyl, $C_1$–$C6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R23$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, or heteroaryl optionally substituted with one or more halogen, $NO_2$, CN, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_5$ is H, $C_1$–$C_3$alkyl or haloalkyl;

$R_6$, $R_9$, $R_{12}$, $R_{17}$, $R_{20}$, $R_{26}$ and $R_{27}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

n is 0 or an integer of 1 or 2;

$R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; and $R_{15}$ and $R_{16}$ are each independently H, $NH_2$, $CH_2CH_2OCH_2CH_2OCH_2CH_2NH_2$ or a $C_1$–$C_6$alkyl group optionally substituted with one or two CN, $OR_5$, $NR_{13}R_{14}$, $CO_2R_{17}$ or $C_3$–$C_7$cycloalkyl group;

phenyl optionally substituted with one or two halogen, $OR_5$, CN, $NR_{13}R_{14}$, $CO_2R_{17}$, $COR_{27}$, an optionally substituted $C_1$–$C_8$alkyl group or an optionally substituted $C_2$–$C_6$alkenyl group;

benzyl optionally substituted with one or two halogen, $OR_5$, $COR_{27}$ or a $C_1$–$C_6$alkyl group optionally substituted with one $OR_5$ or pyridinyl optionally substituted with one or two halogen, $OR_5$, $NR_{13}R_{14}$ or $CO_2R_{17}$ groups or $R_{15}$ and $R_{16}$ may be taken together with the atom to which they are attached to form an optionally substituted 5- to 7-membered ring optionally containing one double bond, a benzofused ring or an additional heteroatom selected from O, N or S; or the stereoisomers thereof or the pharmaceutically acceptable salts thereof.

As used in the specification and claims, the term halogen designates F, Cl, Br or I and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

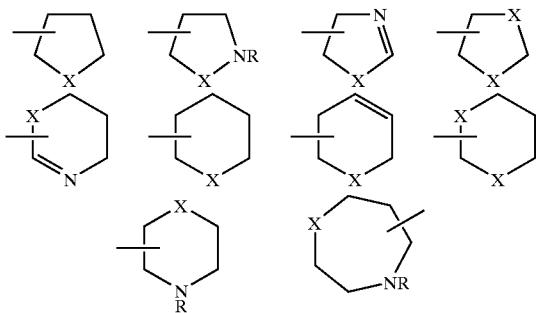

Similarly, as used in the specification and claims, the term heteroaryl designates a $C_5$–$C_{10}$ aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl or cycloalkyl groups, preferably halogen atoms, $NO_2$ or $CF_3$ groups. Typically, 0–3 substituents may be present, preferably 1 or 2. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, nitric, hydrochloric, hydrobromic, citric, malic, maleic, malonic, mandelic, succinic, fumaric, tartaric, propionic, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of the invention are those compounds of formula I wherein $R_3$ is an optionally substituted phenyl or heteroaryl group. Also preferred are those compounds of formula I wherein $R_1$ is H. Another group of preferred compounds of formula I are those compounds wherein $R_4$ is a $C_5$–$C_7$cycloheteroalkyl, heteroaryl or phenyl group each optionally substituted with one or two halogen, CN, $NO_2$, $CF_3$, methoxy, carboxy or $SOR_{26}$ groups.

More preferred compounds of the invention are those compounds of formula I wherein $R_3$ is an optionally substituted phenyl or heteroaryl group and $R_4$ is a thienyl, pyridyl or phenyl group each optionally substituted with one or two halogen, CN, $NO_2$, $CF_3$, methoxy, carboxy or $SOCH_3$ groups. Another group of more preferred compounds of formula I are those compounds wherein $R_2$ is H; $R_3$ is a phenyl group substitued with one or two halogen, $CONR_{15}R_{16}$ or $SO_2NR_{15}R_{16}$ groups; and $R_4$ is a phenyl group substituted with one $NO_2$ or $CF_3$ group.

Examples of the preferred compounds of formula I include:

2-(4-chlorophenyl)-4-[3-(trifluoromethyl)phenyl]-1,2-dihydro-3H-pyrazolo-[3,4-d]thieno[2,3-b]pyridin-3-one;

2-(4-fluorophenyl)-4-[3-(trifluoromethyl)phenyl]-1,2-dihydro-3H-pyrazolo-[3,4-d]thieno[2,3-b]pyridin-3-one;

N-(3,4-dihydroxybenzyl)-3-{3-oxo-4-[3-(trifluoromethyl)phenyl]-3,6-dihydropyrazolo[3,4-d]thieno[2,3-b]pyridin-2(1H)-yl}benzamide;

N-[3-(1-hydroxyethyl)phenyl]-4-{3-oxo-4-[3-(trifluoromethyl)phenyl]-3,6-dihydropyrazolo[3,4-d]thieno[2,3-b]pyridin-2(1H)-yl}benzamide;

({[4-(6-methyl-3-oxo-4-[3-(trifluoromethyl)phenyl]-dihydropyrazolo-[3,4-d]thieno[2,3-b]pyridin-2(1H)-yl)phenyl]sulfonyl}amino)acetic acid;

the stereoisomers thereof; or the pharmaceutically acceptable salts thereof.

Compounds of formula I may be prepared using conventional synthetic methods and, if required, standard separation or isolation techniques.

For example, an aryl, heteroaryl or heterocycloalkyl ester of formula II may undergo a Knoevenagel condensation to give the oxo ester of formula III; said oxo ester is allowed to react with an aminothiophene of formula IV in the presence of a base to give the hydroxythienopyridine of formula V; said hydroxythienopyridine is then converted to the corresponding chloro compound of formula VI via reaction with a chlorinating agent such as thionyl chloride or phosphorous oxychloride; the resultant chloro compound may undergo an addition-elimination reaction with a hydrazine of formula VII to give the hydrazinyl intermediate of formula VIII; and cyclization of the formula VIII compound gives the desired product of formula I. The reaction is illustrated in flow diagram I.

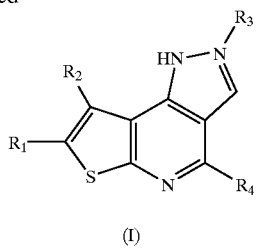

(I)

Cyclization of the intermediates of formula VIII is accomplished in the presence of an acid such as acetic acid or a base such as sodium methoxide or sodium hydride. Alternatively, the chloro intermediate of formula VI may be reacted with hydrazine to give the unsubstituted pyrazolone of formula IX and said pyrazolone may be selectively alkylated with an alkyl or benzyl halide to give those compounds of formula I wherein $R_3$ is an optionally substituted alkyl group (Ia). The reaction is shown in flow diagram II, wherein X is Cl, Br or I.

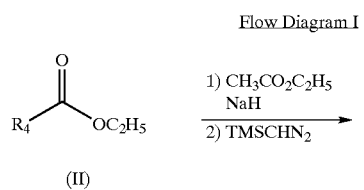

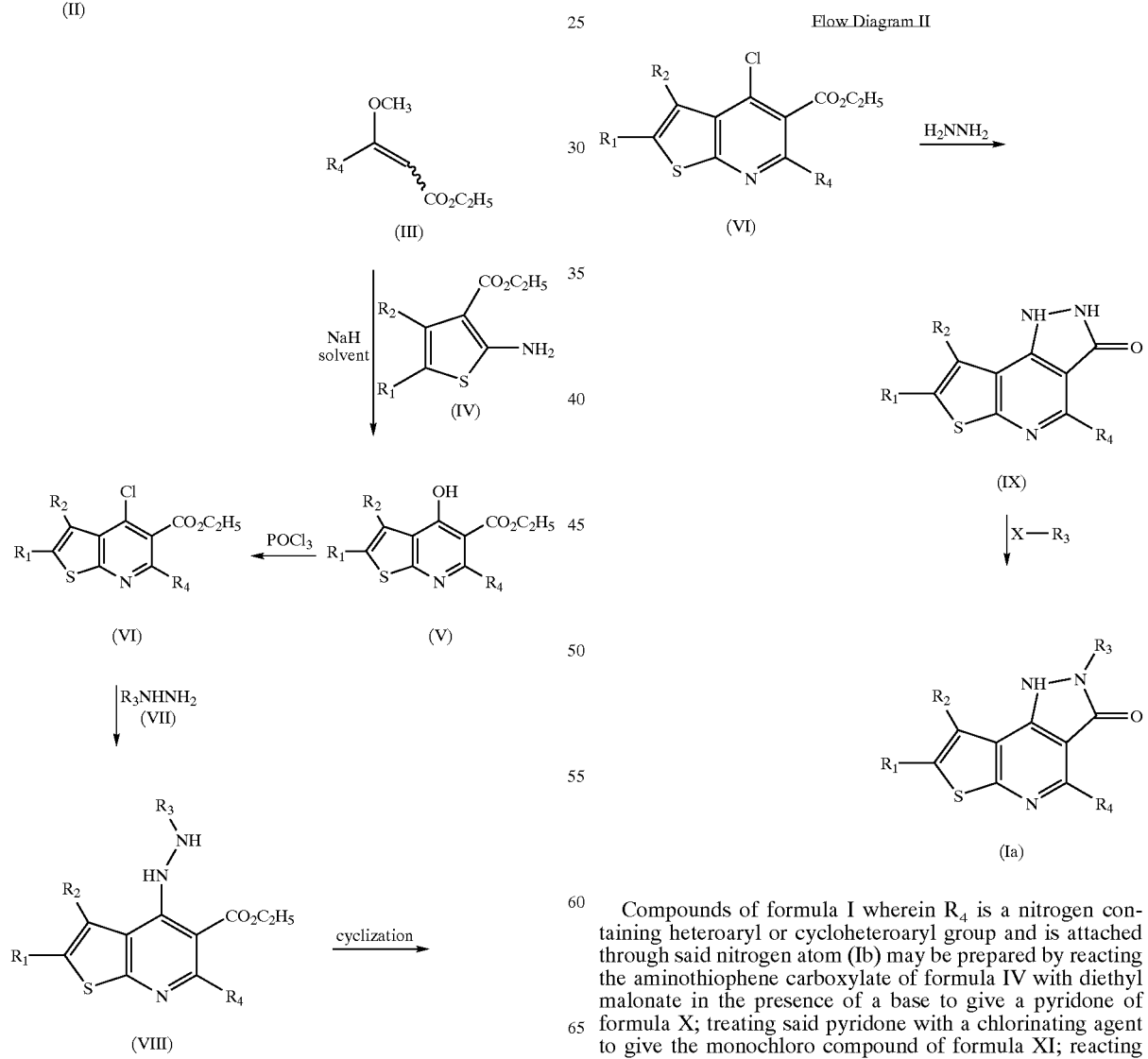

Compounds of formula I wherein $R_4$ is a nitrogen containing heteroaryl or cycloheteroaryl group and is attached through said nitrogen atom (Ib) may be prepared by reacting the aminothiophene carboxylate of formula IV with diethyl malonate in the presence of a base to give a pyridone of formula X; treating said pyridone with a chlorinating agent to give the monochloro compound of formula XI; reacting said monochloro compound with the substituted hydrazine of formula VII to give a hydrazinyl intermediate and cyclizing said intermediate as described in flow diagram I hereinabove to give the di-ketone of formula XII; reacting said di-ketone with a chlorinating agent such as POCl$_3$ to give the di-chloro compound of formula XIII; selectively displacing one chlorine atom with a nucleophile such as an amine or an aniline, R$_4$, and hydrolyzing the second chloro group to give the desired formula Ib product. The reaction is shown in flow diagram III.

ride or tfs anhydride in the presence of a base such as an organic base, i.e. pyridine, triethyl amine or lutidine. The thus-obtained formula XIV compound may undergo an aryl-aryl cross coupling with an aryl boronate or aryl stannate of formula XV in the presence of a catalyst to yield the chloro intermediate of formula VI and said intermediate may then be carried on to those compounds of formula I wherein

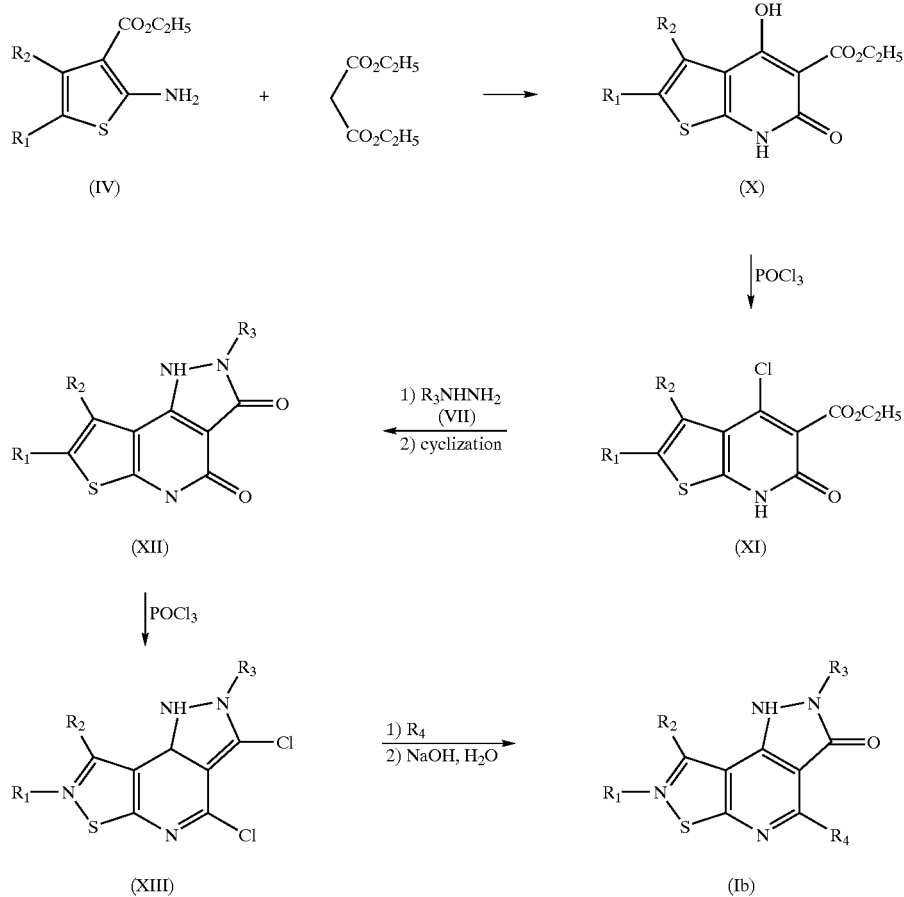

Alternatively, the pyridone intermediate of formula XI may be converted to the trifluoromethylsulfonate of formula XIV via reaction with trifluoromethane sulfonyl (tfs) chlo- R$_4$ is aryl (Ic) as described hereinabove in flow diagram I. The reaction is shown in flow diagram IV wherein M represents B or Sn.

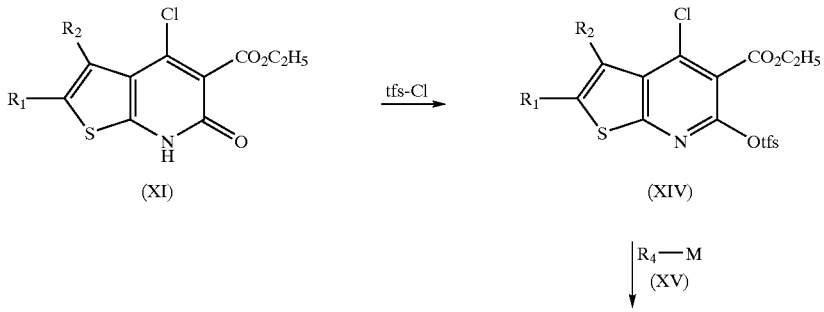

-continued

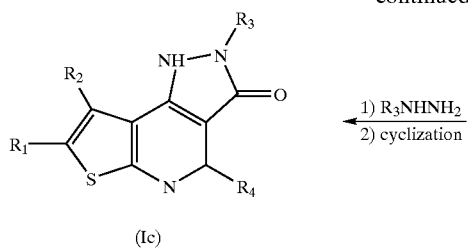

(Ic)

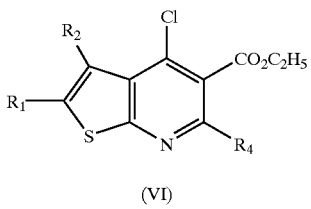

(VI)

Accordingly, the present invention provides a process for the preparation of a compound of formula I which comprises reacting a compound of formula VI with a hydrazine, $R_3NHNH_2$, to form a 4-hydrazinylthieno[2,3-b]pyridine intermediate; and cyclizing said intermediate to give the desired compound of formula I. The process of the invention is illustrated in flow diagram V.

Flow Diagram V

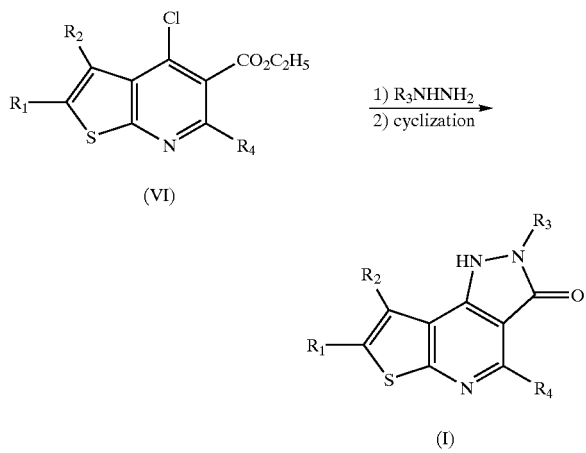

According to the process of the invention, cyclization may be accomplished in the presence of an acid such as acetic acid or in the presence of a base such as sodium hydride, sodium methoxide, sodium t-butoxide or the like, preferably sodium t- butoxide.

Advantageously, the compounds of formula I are useful for the treatment of immune disorders related to or affected by the immune regulatory protein B7-1 such as transplant rejection, graft vs host disease or an autoimmune disease such as multiple sclerosis, rheumatoid arthritis, diabetes mellitus, Grave's disease, pernicious anemia, myasthemia gravis, rheumatic fever, systemic lupus erythematosus, vitiligo, autoimmune Addison's disease, Hashimoto's thyroiditis, Crohn's disease or the like. Accordingly, the present invention provides a method for the treatment of an immune disorder related to or affected by the immune regulatory protein B7-1 which comprises providing a patient in need thereof with an immunotherapeutically effective amount of a compound of formula I as described hereinabove. The compounds may be provided by oral or parenteral administration or in any common manner known to be an effective administration of an immunotherapeutic agent to a patient in need thereof.

The term "providing" as used herein with respect to providing a compound or substance embraced by the invention, designates either directly administering such a compound or substance, or administering a prodrug, derivative or analogue which forms an equivalent amount of the compound or substance within the body.

The immunotherapeutically effective amount provided in the treatment of a specific immune disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula i as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula i compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms EtOAc, THF and DMF designate ethyl acetate, tetrahydrofuran and dimethyl formamide, respectively. All chromatography is performed using $SiO_2$ as support.

EXAMPLE 1

Preparation of Ethyl 3-Methoxy-3-[(trifluoromethyl) phenyl]-2-propenoate

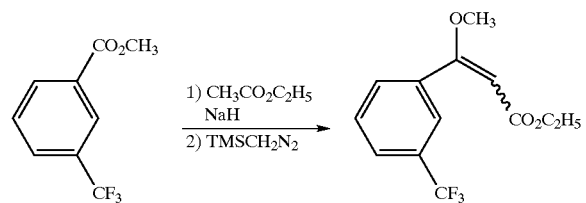

A solution of methyl 3-trifluoromethylbenzoate (62.0 g, 0.3 mol) in EtOAc is treated with NaH (60% in mineral oil, 8.4 g), and gently heated at 40° C. until a mild exotherm occurs. After the cessation of reflux, additional NaH is added (12.7 g, total of 0.6 mol) and the resultant mixture is heated at reflux temperature for 16 h, cooled to room temperature and diluted with methylene chloride and water. The organic phase is separated, washed with brine, dried over $Na_2SO_4$ and concentrated in vacuo to give an oil residue. The oil is treated with acetonitrile and methanol followed by a solution of $TMSCH_2N_2$ in hexanes (300 mL, 2M, 0.6 mol), stirred for 36 h and treated with aqueous 5% HCl. After nitrogen evolution ceases, the organic layer is separated, washed with brine, dried over $Na_2SO_4$ and concentrated in vacuo. The resultant residue is chromatographed through a plug of silica gel (4:1, hexanes: EtOAc) to give the title compound as a white solid, 65.5 g, (78% yield). This product is used as is in Example 2.

EXAMPLE 2

Preparation of Ethyl 4-Chloro-1-methyl-6-[3-(trifluoromethyl)phenyl]-thieno-[2,3-b]pyridine-5-carboxylate

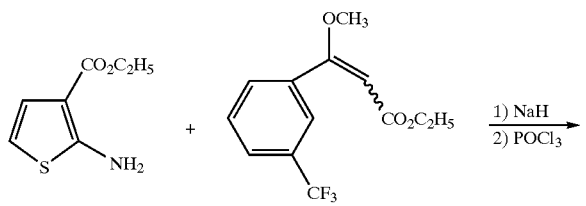

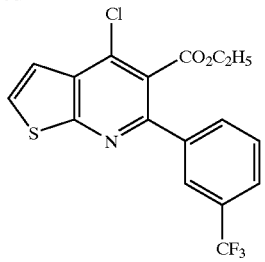

A solution of ethyl 3-methoxy-3-[(trifluoromethyl) phenyl]-2-propenoate (1.60 g, 6.14 mmol) and methyl 3-amino-2-thiophenecarboxylate (1.04 g, 6.14 mmol) in THF at 0° C. is treated with NaH (60% dispersion in mineral oil, 501 mg, 12.5 mmol), heated at reflux temperature for 15 h, cooled to 0° C., quenched with aqueous $NH_4Cl$ and extracted with EtOAc. The extracts are combined, washed with water, dried over $MgSO_4$ and concentrated in vacuo to afford the title product as a tan powder in quantitative yield, identified by HNMR and mass spectral analyses.

EXAMPLE 3

Preparation of 2-(4-Fluorophenyl)-4-[3-(trifluoromethyl) phenyl]1,2-dihydro-3H-pyrazolo[3,4-d]thieno[2,3-b] pyridin-3-one

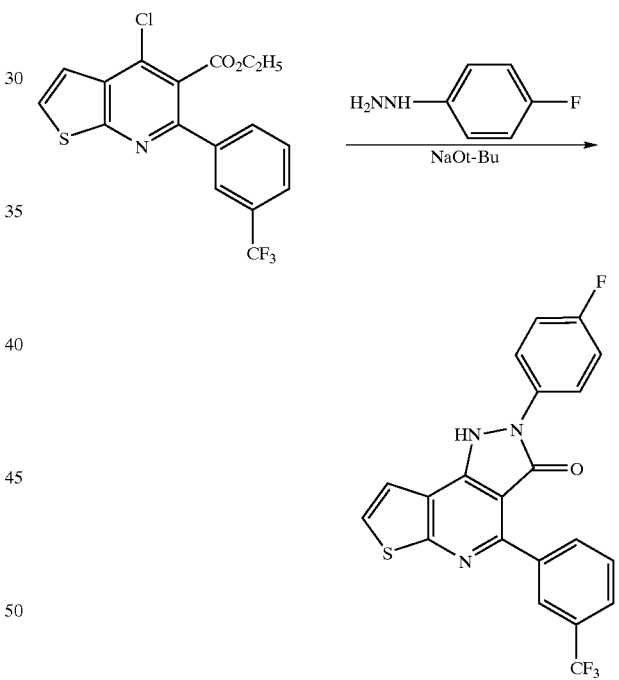

A solution of ethyl 4-chloro-1-methyl-6-[3-(trifluoromethyl)phenyl]thieno-[2,3b]pyridine-5-carboxylate (255 mg, 0.686 mmol) and 4-(fluorophenyl) hydrazine hydrochloride (250 mg, 2.06 mmol) in ethanol is heated at reflux temperature for 16 h, cooled to room temperature and concentrated in vacuo. The resultant residue is chromatographed (silica gel, $EtOAc/CH_2Cl_2$/hexanes:15/15/70) to afford the hydrazino intermediate as a yellow solid, 80 mg. A solution of this hydrazino intermediate (69 mg, 0.15 mmol) in ethanol at 0° C. is treated with NaH (60% dispersion in mineral oil, 17 mg, 0.45 mmol), heated at reflux temperature for 2 h, cooled to 40° C., held at 40° C. for 2.5 days, poured onto ice and neutralized to pH 8 with $NH_4Cl$ and filtered. The filtercake is washed with water and dried in vacuo to afford the title product as a white powder, 45 mg, identified by HNMR and mass spectral analyses.

EXAMPLES 4–7
Preparation of Pyrazolo[3,4-d]thieno[2,3-b]pyridinone Derivatives

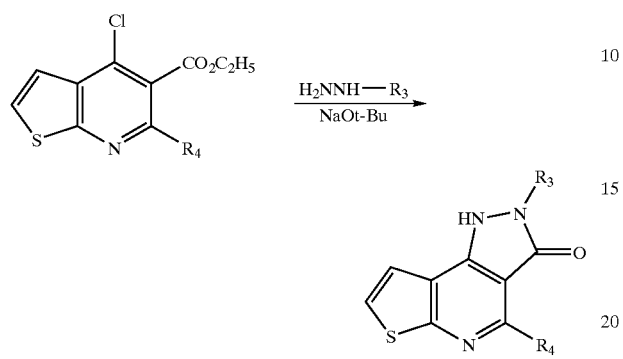

Using essentially the same procedure described in Example 3 hereinabove and employing the appropriate thienopyridine substrate and desired hydrazine, the compounds shown in Table I are obtained and identified by HNMR and mass spectral analyses.

TABLE I

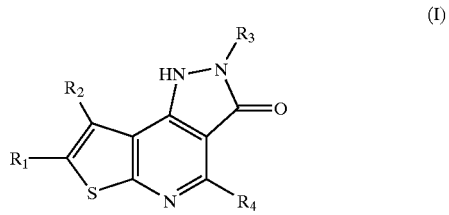

| Ex. No. | R3 | R4 | [M + H] |
|---|---|---|---|
| 4 | 4-ClC$_6$H$_4$ | 3-CF$_3$C$_6$H$_4$ | 445.852 |
| 5 | 4-HN[3-(1-hydroxyethyl)phenyl]COC$_6$H$_4$ | 3-CF$_3$C$_6$H$_4$ | — |
| 6 | 3-HN(3,4-dihydroxybenzyl)COC$_6$H$_4$ | 3-CF$_3$C$_6$H$_4$ | — |
| 7 | 4-HN(CH$_2$CO$_2$H)SO$_2$C$_6$H$_4$ | 3-CF$_3$C$_6$H$_4$ | — |

EXAMPLE 7
Evaluation of B7-1/CD28 Binding Inhibition for Test Compounds
CD28/B7-1 ELISA Wells are coated with 300 ng CD28-Fc in carbonate buffer (pH 9.4) overnight at 4° C., blocked with 1% bovine serum albumin in tris-buffered saline (TBS) for 1 h at 22° C. and washed 3 times in TBS prior to assay. The detection complex is formed as follows: B7-1-Fc-biotin, prepared using NHS-LC-biotin (Pierce #21335) according to the manufacturers instructions (4.1 moles biotin/mole Fc), is added at 0.8 ug/ml to streptavidin-alkaline phosphatase (Caltag Sa1008 at 1:1000 in TBS. Gradient dilutions of test compound in dimethylsulfoxide (1% final) are added to this complex and incubated 30 min. at 22° C. Detection complex (+/− inhibitors) is then added to the CD28 coated wells for 25 min. at 22° C., washed 5 times with TBS, developed with the calorimetric substrate pNPP (Pierce #34045) in diethanolamine/MgCl$_2$ buffer (pH 9.5) and read at 405 nm. The inhibition constant (IC$_{50}$) is calculated by subtracting the background binding and comparing to uninhibited (DMSO alone) controls. The inhibition constant represents the concentration of test compound required to achieve 50% inhibition. The results are shown in Table II.

TABLE II

| Example Number | B7-1/CD28 Inhibition IC50 (nM) |
|---|---|
| 3 | 600 |
| 4 | 500 |
| 5 | — |
| 6 | — |
| 7 | — |

What is claimed is:
1. A compound of formula I:

(I)

wherein
R$_1$ and R$_2$ are each independently H, C$_1$–C$_{10}$alkyl optionally substituted with one or more halogen, hydroxy, C$_1$–C$_4$alkoxy, CO$_2$R$_6$, CONR$_7$R$_8$, C$_3$–C$_7$cycloalkyl or optionally substituted phenyl groups, or
phenyl optionally substituted with one to three halogen, hydroxy, C$_1$–C$_6$haloalkyl, C$_1$–C$_4$alkoxy, CO$_2$R$_9$, NR$_{10}$R$_{11}$ or CN groups;
R$_3$ is H, C$_1$–C$_6$alkyl optionally substituted with a phenyl, naphthyl or C$_5$–C$_{10}$ heteroaryl ring system containing 1, 2 or 3 heteroatoms selected from N, O or S group each group optionally substituted with one to three C$_1$–C$_6$alkyl, C$_1$–C$_6$haloalkyl, C$_1$–C$_4$alkoxy, hydroxy, CHO, NO$_2$, CN, CO$_2$R$_{12}$ or NR$_{13}$R$_{14}$ groups,
phenyl optionally substituted with one to three halogen, NO$_2$, CN, hydroxy, C$_1$–C$_6$alkyl, C$_1$–C$_6$haloalkyl, C$_1$–C$_6$alkoxy, phenyl, phenoxy, benzyl, benzyloxy, CONR$_{15}$R$_{16}$, SO$_2$NR$_{15}$R$_{16}$, CO$_2$R$_{17}$, NR$_{18}$R$_{19}$ or CH$_2$CO$_2$R$_{20}$ groups,
naphthyl optionally substituted with one to three halogen, NO$_2$, CN, hydroxy, C$_1$–C$_6$alkyl, C$_1$–C$_6$haloalkyl, C$_1$–C$_6$alkoxy, phenyl, phenoxy, benzyl, benzyloxy, CO$_2$R$_{17}$, NR$_{18}$R$_{19}$ or CH$_2$CO$_2$R$_{20}$ groups,
C$_5$–C$_7$cycloheteroalkyl ring system containing 1 or 2 heteroatoms selected from N, O or S optionally containing one double bond and optionally substituted with one to three halogen, NO$_2$, CN, C$_1$–C$_6$alkyl, C$_1$–C$_6$haloalkyl, C$_1$–C$_4$alkoxy, CO$_2$R$_{17}$ or NR$_{18}$R$_{19}$ groups, or
C$_5$–C$_{10}$ heteroaryl ring system containing 1, 2 or 3 heteroatoms selected from N, O or S optionally substituted with one to three halogen, NO$_2$, CN, C$_1$–C$_6$alkyl, C$_1$–C$_6$haloalkyl, C$_1$–C$_4$alkoxy, CO$_2$R$_{17}$ or NR$_{18}$R$_{19}$ groups;
R$_4$ is phenyl optionally substituted with one to three halogen, NO$_2$, CN, hydroxy, C$_1$–C$_6$alkyl, C$_1$–C$_6$alkylthio, C$_1$–C$_6$haloalkyl, C$_1$–C$_6$alkoxy, phenyl, phenoxy, benzyl, benzyloxy, SO$_n$R$_{26}$, SO$_2$NR$_{21}$R$_{22}$, CO$_2$R$_{23}$ or NR$_{24}$R$_{25}$ groups,
C$_5$–C$_7$cycloheteroalkyl ring system containing 1 or 2 heteroatoms selected from N, O or S optionally containing one double bond and optionally substituted with one or more halogen, $NO_2$, CN, hydroxy, $C_1-C_6$alkyl, $C_1-C_6$alkylthio, $C_1-C_6$haloalkyl, $C_1-C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, or $C_5-C_{10}$ heteroaryl ring system containing 1, 2 or 3 heteroatoms selected from N, O or S optionally substituted with one or more halogen, $NO_2$, CN, hydroxy, $C_1-C_6$alkyl, $C_1-C_6$alkylthio, $C_1-C_6$haloalkyl, $C_1-C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_5$ is H, $C_1-C_3$alkyl or haloalkyl;

$R_6$, $R_9$, $R_{12}$, $R_{17}$, $R_{20}$, $R_{26}$ and $R_{27}$ are each independently H or a $C_1-C_6$alkyl, $C_3-C_7$cycloalkyl, $C_1-C_6$haloalkyl, phenyl, $C_5-C_7$cycloheteroalkyl ring system containing 1 or 2 heteroatoms selected from N, O or S optionally containing one double bond or $C_5-C_{10}$ heteroaryl ring system containing 1, 2 or 3 heteroatoms selected from N, O or S group each optionally substituted;

n is 0 or an integer of 1 or 2;

$R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1-C_6$alkyl, $C_3-C_7$cycloalkyl, $C_1-C_6$haloalkyl, phenyl, $C_5-C_7$cycloheteroalkyl ring system containing 1 or 2 heteroatoms selected from N, O or S optionally containing one double bond or $C_5-C_{10}$ heteroaryl ring system containing 1, 2 or 3 heteroatoms selected from N, O or S group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; and $R_{15}$ and $R_{16}$ are each independently H, $NH_2$, $CH_2CH_2OCH_2CH_2OCH_2CH_2NH_2$ or a $C_1-C_6$alkyl group optionally substituted with one or two CN, $OR_5$, $NR_{13}R_{14}$, $CO_2R_{17}$ or $C_3-C_7$cycloalkyl group;

phenyl optionally substituted with one or two halogen, $OR_5$, CN, $NR_{13}R_{14}$, $CO_2R_{17}$, $COR_{27}$, an optionally substituted $C_1-C_8$alkyl group or an optionally substituted $C_2-C_6$alkenyl group;

benzyl optionally substituted with one or two halogen, $OR_5$, $COR_{27}$ or a $C_1-C_6$alkyl group optionally substituted with one $OR_5$ or pyridinyl optionally substituted with one or two halogen, $OR_5$, $NR_{13}R_{14}$ or $CO_2R_{17}$ groups or $R_{15}$ and $R_{16}$ may be taken together with the atom to which they are attached to form an optionally substituted 5- to 7-membered ring optionally containing one double bond, a benzofused ring or an additional heteroatom selected from O, N or S; or the pharmaceutically acceptable salts thereof.

2. The compound according to claim 1 wherein $R_3$ is an optionally substituted phenyl or heteroaryl group.

3. The compound according to claim 1 wherein $R_1$ and $R_2$ are H.

4. The compound according to claim 1 wherein $R_4$ is a $C_5-C_7$cycloheteroalkyl, heteroaryl or phenyl group each optionally substituted with one or two halogen, CN, $NO_2$, $CF_3$, methoxy, carboxy or $SOR_{26}$ groups.

5. The compound according to claim 2 wherein $R_1$ and $R_2$ are H.

6. The compound according to claim 2 wherein $R_4$ is a thienyl, pyridyl or phenyl group, each optionally substituted with one or two halogen, CN, $NO_2$, $CF_3$, methoxy, carboxy or $SOCH_3$ groups.

7. The compound according to claim 3 wherein $R_3$ is a phenyl group substituted with one or two halogen, $CONR_{15}R_{16}$ or $SO_2NR_{15}R_{16}$ groups.

8. The compound according to claim 7 wherein $R_4$ is a phenyl group substituted with one $NO_2$ or $CF_3$ group.

9. The compound according to claim 1 selected from the group consisting of:

2-(4-chlorophenyl)-4-[3-(trifluoromethyl)phenyl]-1,2-dihydro-3H-pyrazolo-[3,4-d]thieno[2,3-b]pyridin-3-one;

2-(4-fluorophenyl)-4-[3-(trifluoromethyl)phenyl]-1,2-dihydro-3H-pyrazolo-[3,4-d]thieno[2,3-b]pyridin-3-one;

N-(3,4-dihydroxybenzyl)-3-{3-oxo-4-[3-(trifluoromethyl)phenyl]-3,6-dihydropyrazolo[3,4-d]thieno[2,3-b]pyridin-2(1H)-yl}benzamide;

N-[3-(1-hydroxyethyl)phenyl]-4-{3-oxo-4-[3-(trifluoromethyl)phenyl]-3,6-dihydropyrazolo[3,4-d]thieno[2,3-b]pyridin-2(1H)-yl}benzamide;

({[4-(6-methyl-3-oxo-4-[3-(trifluoromethyl)phenyl]-dihydropyrazolo-[3,4-d]thieno[2,3-b]pyridin-2-(1H)-yl)phenyl]sulfonyl}amino)acetic acid; and the pharmaceutically acceptable salts thereof.

10. A method for the treatment of an immune disorder related to or affected by the immune regulatory protein B7-1 which comprises providing a patient in need thereof an immunotherapeutically effective amount of a compound of formula I:

(I)

wherein $R_1$ and $R_2$ are each independently H, $C_1-C_{10}$alkyl optionally substituted with one or more halogen, hydroxy, $C_1-C_4$alkoxy, $CO_2R_6$, $CONR_7R_8$, $C_3-C_7$cycloalkyl or optionally substituted phenyl groups, or phenyl optionally substituted with one to three halogen, hydroxy, $C_1-C_6$haloalkyl, $C_1-C_4$alkoxy, $CO_2R_9$, $NR_{10}R_{11}$ or CN groups;

$R_3$ is H, $C_1-C_6$alkyl optionally substituted with a phenyl, naphthyl or $C_5-C_{10}$ heteroaryl ring system containing 1, 2 or 3 heteroatoms selected from N, O or S group each group optionally substituted with one to three $C_1-C_6$alkyl, $C_1-C_6$haloalkyl, $C_1-C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1-C_6$alkyl, $C_1-C_6$haloalkyl, $C_1-C_6$alkoxy, phenyl, phenoxy, benzyl, benzyloxy, $CONR_{15}R_{16}$, $SO_2NR_{15}R_{16}$, $CO_2R_{17}$, $NR_{18}R_{19}$ or $CH_2CO_2R_{20}$ groups, naphthyl optionally substituted with one to three halogen, $NO_2$, CN, hydroxy, $C_1-C_6$alkyl, $C_1-C_6$haloalkyl, $C_1-C_6$alkoxy, phenyl, phenoxy, benzyl, benzyloxy, $CO_2R_{17}$, $NR_{18}R_{19}$ or $CH_2CO_2R_{20}$ groups, $C_5-C_7$cycloheteroalkyl ring system containing 1 or 2 heteroatoms selected from N, O or S optionally containing one double bond and optionally substituted with one to three halogen, $NO_2$, CN, $C_1-C_6$alkyl, $C_1-C_6$haloalkyl, $C_1-C_4$alkoxy, $CO_2R_{17}$ or $NR_{18}R_{19}$ groups, or $C_5-C_{10}$ heteroaryl ring system containing 1, 2 or 3 heteroatoms selected from N, O or S optionally substituted with one to three halogen, NO₂, CN, C₁–C₆alkyl, C₁–C₆haloalkyl, C₁–C₄alkoxy, CO₂R₁₇ or NR₁₈R₁₉ groups;

R₄ is phenyl optionally substituted with one to three halogen, NO₂, CN, hydroxy, C₁–C₆alkyl, C₁–C₆alkylthio, C₁–C₆haloalkyl, C₁–C₆alkoxy, phenyl, phenoxy, benzyl, benzyloxy, SO$_n$R₂₆, SO₂NR₂₁R₂₂, CO₂R₂₃ or NR₂₄R₂₅ groups, cycloheteroalkyl ring system containing 1 or 2 heteroatoms selected from N, O or S optionally containing one double bond and optionally substituted with one or more halogen, NO₂, CN, hydroxy, C₁–C₆alkyl, C₁–C₆alkylthio, C₁–C₆haloalkyl, C₁–C₆alkoxy, phenyl, phenoxy, benzyl, benzyloxy, SO$_n$R₂₆, SO₂NR₂₁R₂₂, CO₂R₂₃ or NR₂₄R₂₅ groups, or C₅–C₁₀ heteroaryl ring system containing 1, 2 or 3 heteroatoms selected from N, O or S optionally substituted with one or more halogen, NO₂, CN, hydroxy, C₁–C₆alkyl, C₁–C₆alkylthio, C₁–C₆haloalkyl, C₁–C₆alkoxy, phenyl, phenoxy, benzyl, benzyloxy, SO$_n$R₂₆, SO₂NR₂₁R₂₂, CO₂R₂₃ or NR₂₄R₂₅ groups;

R₅ is H, C₁–C₃alkyl or haloalkyl;

R₆, R₉, R₁₂, R₁₇, R₂₀, R₂₆ and R₂₇ are each independently H or a C₁–C₆alkyl, C₃–C₇ cycloalkyl, C₁–C₆haloalkyl, phenyl, C₅–C₇cycloheteroalkyl ring system containing 1 or 2 heteroatoms selected from N, O or S optionally containing one double bond or C₅–C₁₀ heteroaryl ring system containg 1, 2 or 3 heteroatoms selected from N, O or S group each optionally substituted;

n is 0 or an integer of 1 or 2;

R₇, R₈, R₁₀, R₁₁, R₁₃, R₁₄, R₁₈, R₁₉, R₂₁, R₂₂, R₂₄ and R₂₅ are each independently H or a C₁–C₆alkyl, C₃–C₇cycloalkyl, C₁–C₆haloalkyl, phenyl, C₅–C₇cycloheteroalkyl ring system containing 1 or 2 heteroatoms selected from N, O or S optionally containing one double bond or C₅–C₁₀ heteroaryl ring system containing 1, 2 or 3 heteroatoms selected from N, O or S group each optionally substituted or each of R₇ and R₈ or R₁₀ and R₁₁ or R₁₃ and R₁₄ or R₁₈ and R₁₉ or R₂₁ and R₂₂ or R₂₄ and R₂₅ may be taken together with the nitrogen atom to which they are attached to form a 5- to 7-membered ring optionally containing another heteroatom selected from O, N or S; and R₁₅ and R₁₆ are each independently H, NH₂, CH₂CH₂OCH₂CH₂OCH₂CH₂NH₂ or a C₁–C₆alkyl group optionally substituted with one or two CN, OR₅, NR₁₃R₁₄, CO₂R₁₇ or C₃–C₇cycloalkyl group;

phenyl optionally substituted with one or two halogen, OR₅, CN, NR₁₃R₁₄, CO₂R₁₇, COR₂₇, an optionally substituted C₁–C₈alkyl group or an optionally substituted C₂–C₆alkenyl group;

benzyl optionally substituted with one or two halogen, OR₅, COR₂₇ or a C₁–C₆alkyl group optionally substituted with one OR₅ or pyridinyl optionally substituted with one or two halogen, OR₅, NR₁₃R₁₄ or CO₂R₁₇ groups or R₁₅ and R₁₆ may be taken together with the atom to which they are attached to form an optionally substituted 5- to 7-membered ring optionally containing one double bond, a benzofused ring or an additional heteroatom selected from O, N or S; or the pharmaceutically acceptable salts thereof.

11. The method according to claim 10 wherein said disorder is transplant rejection.

12. The method according to claim 10 wherein said disorder is an autoimmune disease.

13. The method according to claim 10 wherein said disorder is graft vs. host disease.

14. The method according to claim 12 wherein said disease is multiple sclerosis or rheumatoid arthritis.

15. A pharmaceutical composition which comprises a pharmaceutically acceptable carrier and an effective amount of a compound of formula I:

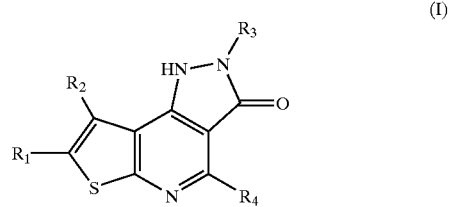

(I)

wherein

R₁ and R₂ are each independently H, C₁–C₁₀alkyl optionally substituted with one or more halogen, hydroxy, C₁–C₄alkoxy, CO₂R₆, CONR₇R₈, C₃C₇cycloalkyl or optionally substituted phenyl groups, or phenyl optionally substituted with one to three halogen, hydroxy, C₁–C₆haloalkyl, C₁–C₄alkoxy, CO₂R₉, NR₁₀R₁₁ or CN groups;

R₃ is H, C₁–C₆alkyl optionally substituted with a phenyl, naphthyl or C₅–C₁₀ heteroaryl ring system containing 1, 2 or 3 heteroatoms selected from N, O or S group each group optionally substituted with one to three C₁–C₆alkyl, C₁–C₆haloalkyl, C₁–C₄alkoxy, hydroxy, CHO, NO₂, CN, CO₂R₁₂ or NR₁₃R₁₄ groups, phenyl optionally substituted with one to three halogen, NO₂, CN, hydroxy, C₁–C₆alkyl, C₁–C₆haloalkyl, C₁–C₆alkoxy, phenyl, phenoxy, benzyl, benzyloxy, CONR₁₅R₁₆, SO₂NR₁₅R₁₆, CO₂R₁₇, NR₁₈R₁₉ or CH₂CO₂R₂₀ groups, naphthyl optionally substituted with one to three halogen, NO₂, CN, hydroxy, C₁–C₆alkyl, C₁–C₆haloalkyl, C₁–C₆alkoxy, phenyl, phenoxy, benzyl, benzyloxy, CO₂R₁₇, NR₁₈R₁₉ or CH₂CO₂R₂₀ groups, C₅–C₇cycloheteroalkyl ring system containing 1 or 2 heteroatoms selected from N, O or S optionally containing one double bond and optionally substituted with one to three halogen, NO₂, CN, C₁–C₆alkyl, C₁–C₆haloalkyl, C₁–C₄alkoxy, CO₂R₁₇ or NR₁₈R₁₉ groups, or C₅–C₁₀ heteroaryl ring system containing 1, 2 or 3 heteroatoms selected from N, O or S optionally substituted with one to three halogen, NO₂, CN, C₁–C₆alkyl, C₁–C₆haloalkyl, C₁–C₄alkoxy, CO₂R₁₇ or NR₁₈R₁₉ groups;

R₄ is phenyl optionally substituted with one to three halogen, NO₂, CN, hydroxy, C₁–C₆alkyl, C₁–C₆alkylthio, C₁–C₆haloalkyl, C₁–C₆alkoxy, phenyl, phenoxy, benzyl, benzyloxy, SO$_n$R₂₆, SO₂NR₂₁R₂₂, CO₂R₂₃ or NR₂₄R₂₅ groups, C₅–C₇cycloheteroalkyl ring system containing 1, 2 or 3 heteroatoms selected from N, O or S optionally containing one double bond and optionally substituted with one or more halogen, NO₂, CN, hydroxy, C₁–C₆alkyl, C₁–C₆alkylthio, C₁–C₆haloalkyl, C₁–C₆alkoxy, phenyl, phenoxy, benzyl, benzyloxy, SO$_n$R₂₆, SO₂NR₂₁R₂₂, CO₂R₂₃ or NR₂₄R₂₅ groups, or C₅–C₁₀ heteroaryl ring system containing 1, 2 or 3 heteroatoms selected from N, O or S optionally substituted with one or more halogen, NO₂, CN, hydroxy, C₁–C₆alkyl, C₁–C₆alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_5$ is H, $C_1$–$C_3$alkyl or haloalkyl;

$R_6$, $R_9$, $R_{12}$, $R_{17}$, $R_{20}$, $R_{26}$ and $R_{27}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl ring system containing 1 or 2 heteroatoms selected from N, O or S heteroatoms selected from N, O or S optionally containing one double bond or $C_5$–$C_{10}$ heteroaryl ring system containing 1, 2 or 3 heteroatoms selected from N, O or S group each optionally substituted;

n is 0 or an integer of 1 or 2;

$R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl ring system containing 1 or 2 heteroatoms selected from N, O or S optionally containing one double bond or $C_5$–$C_{10}$ heteroaryl ring system containing 1, 2 or 3 heteroatoms selected from N, O or S group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; and $R_{15}$ and $R_{16}$ are each independently H, $NH_2$, $CH_2CH_2OCH_2CH_2OCH_2CH_2NH_2$ or a $C_1$–$C_6$alkyl group optionally substituted with one or two CN, $OR_5$, $NR_{13}R_{14}$, $CO_2R_{17}$ or $C_3$–$C_7$cycloalkyl group;

phenyl optionally substituted with one or two halogen, $OR_5$, CN, $NR_{13}R_{14}$, $CO_2R_{17}$, $COR_{27}$, an optionally substituted $C_1$–$C_8$alkyl group or an optionally substituted $C_2$–$C_6$alkenyl group;

benzyl optionally substituted with one or two halogen, $OR_5$, $COR_{27}$ or a $C_1$–$C_6$alkyl group optionally substituted with one $OR_5$ or pyridinyl optionally substituted with one or two halogen, $OR_5$, $NR_{13}R_{14}$ or $CO_2R_{17}$ groups or $R_{15}$ and $R_{16}$ may be taken together with the atom to which they are attached to form an optionally substituted 5- to 7-membered ring optionally containing one double bond, a benzofused ring or an additional heteroatom selected from O, N or S; or the pharmaceutically acceptable salts thereof.

16. The composition according to claim 15 having a formula I compound wherein $R_3$ is an optionally substituted phenyl, thienyl or pyridyl group.

17. The composition according to claim 16 having a formula I compound wherein $R_1$ and $R_2$ are H.

18. The composition according to claim 17 having a formula I compound wherein $R_4$ is a thienyl, pyridyl or phenyl group each optionally substituted with one or two halogen, CN, $NO_2$, $CF_3$, methoxy, carboxy or $SOCH_3$ groups.

19. The composition according to claim 18 having a formula I compound wherein $R_3$ is a phenyl group substituted with one or two halogen, $CONR_{15}R_{16}$ or $SO_2NR_{15}R_{16}$ groups.

20. A process for the preparation of a compound of formula I:

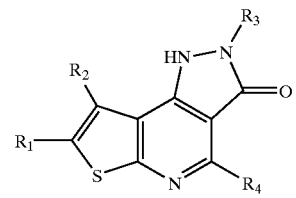

wherein $R_1$ and $R_2$ are each independently H, $C_1$–$C_{10}$alkyl optionally substituted with one or more halogen, hydroxy, $C_1$–$C_4$alkoxy, $CO_2R_6$, $CONR_7R_8$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_9$, $NR_{10}R_{11}$ or CN groups;

$R_3$ is H, $C_1$–$C_6$alkyl optionally substituted with a phenyl, naphthyl or $C_5$–$C_{10}$ heteroaryl ring system containing 1, 2 or 3 heteroatoms selected from N, O or S group each group optionally substituted with one to three $C_1$–$C_6$alkyl, $C_1$–$C_6$haloalkyl, $C_1$–$C_4$alkoxy, hydroxy, CHO, $NO_2$, CN, $CO_2R_{12}$ or $NR_{13}R_{14}$ groups, phenyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CONR_{15}R_{16}$, $SO_2NR_{15}R_{16}$, $CO_2R_{17}$, $NR_{18}R_{19}$ or $CH_2CO_2R_{20}$ groups, naphthyl optionally substituted with one to three halogen, $NO_2$, CN, hydroxy, $C_1$–$C_6$alkyl, $C_1$–$C_6$haloalkyl, $C_1$–$C_6$alkoxy, phenyl, phenoxy, benzyl, benzyloxy, $CO_2R_{17}$, $NR_{18}R_{19}$ or $CH_2CO_2R_{20}$ groups, $C_5$–$C_7$cycloheteroalkyl ring system containing 1, 2 or 3 heteroatoms selected from N, O or S optionally containing one double bond and optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups, or $C_5$–$C_{10}$ heteroaryl ring system containing 1, 2 or 3 heteroatoms selected from N, O or S optionally substituted with one to three halogen, $NO_2$, CN, $C_1$–$C_6$alkyl, $C_1$–$C_6$haloalkyl, $C_1$–$C_4$alkoxy, $CO_2R_{17}$ or $NR_{18}R_{19}$ groups;

$R_4$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups, $C_5$–$C_7$cycloheteroalkyl ring system containing 1, 2 or 3 heteroatoms selected from N, O or S optionally containing one double bond and optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}$,$R_{22}$, $CO_2R_{23}$ or $NR_{24}R_{25}$ groups, or $C_5$–$C_{10}$ heteroaryl ring system containing 1, 2 or 3 heteroatoms selected from N, O or S optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{26}$, $SO_2NR_{21}R_{22}$, $CO_2R_{23}$ or $NR_{24}R_{25}$ groups;

$R_5$ is H, $C_1$–$C_3$alkyl or haloalkyl;

$R_6$, $R_9$, $R_{12}$, $R_{17}$, $R_{20}$, $R_{26}$ and $R_{27}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl ring system containing 1 or 2 heteroatoms selected from N, O or S optionally containing one double bond or $C_5$–$C_{10}$ heteroaryl ring system containing 1, 2 or 3 heteroatoms selected from N, O or S group each optionally substituted;

n is 0 or an integer of 1 or 2;

$R_7$, $R_8$, $R_{10}$, $R_{11}$, $R_{13}$, $R_{14}$, $R_{18}$, $R_{19}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalky ring system containing 1 or 2 heteroatoms selected from N, O or S optionally containing one double bond or $C_5$–$C_{10}$ heteroaryl ring system containing 1, 2 or 3 heteroatoms selected from N, O or S group each optionally substituted or each of $R_7$ and $R_8$ or $R_{10}$ and $R_{11}$ or $R_{13}$ and $R_{14}$ or $R_{18}$ and $R_{19}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S; and $R_{15}$ and $R_{16}$ are each independently H, $NH_2$, $CH_2CH_2OCH_2CH_2OCH_2CH_2NH_2$ or a $C_1$–$C_6$alkyl group optionally substituted with one or two CN, $OR_5$, $NR_{13}R_{14}$, $CO_2R_{17}$ or $C_3$–$C_7$cycloalkyl group;

phenyl optionally substituted with one or two halogen, $OR_5$, CN, $NR_{13}R_{14}$, $CO_2R_{17}$, $COR_{27}$, an optionally substituted $C_1$–$C_8$alkyl group or an optionally substituted $C_2$–$C_6$alkenyl group;

benzyl optionally substituted with one or two halogen, $OR_5$, $COR_{27}$ or a $C_1$–$C_6$alkyl group optionally substituted with one $OR_5$ or pyridinyl optionally substituted with one or two halogen, $OR_5$, $NR_{13}R_{14}$ or $CO_2R_{17}$ groups or $R_{15}$ and $R_{16}$ may be taken together with the atom to which they are attached to form an optionally substituted 5- to 7-membered ring optionally containing one double bond, a benzofused ring or an additional heteroatom selected from O, N or S; or which process comprises reacting a compound of formula VI:

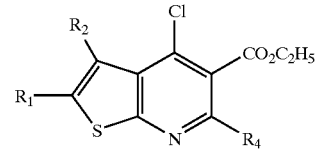

(VI)

wherein $R_1$, $R_2$ and $R_4$ are described hereinabove with a hydrazine, $R_3NHNH_2$, to give a 3-hydrazinylthieno-[2,3-b]pyridine intermediate; and cyclizing said intermediate to give the desired compound of formula I.

* * * * *